(12) United States Patent
Sherony et al.

(10) Patent No.: US 10,597,835 B2
(45) Date of Patent: Mar. 24, 2020

(54) SURROGATE FOR CONCRETE DIVIDER

(71) Applicants: Toyota Motor Engineering & Manufacturing North America, Inc., Plano, TX (US); The Trustees of Indiana University, Indianapolis, IN (US); Ohio State Innovation Foundation, Columbus, OH (US)

(72) Inventors: Rini Sherony, Ann Arbor, MI (US); Stanley Yung-Ping Chien, Zionsville, IN (US); Qiang Yi, Carmel, IN (US); Jun Lin, Carmel, IN (US); Abir Saha, Chicago, IL (US); Yaobin Chen, Carmel, IN (US); Chi-Chih Chen, Dublin, OH (US)

(73) Assignees: Toyota Motor Engineering & Manufacturing North America, Inc., Plano, TX (US); The Trustees of Indiana University, Indianapolis, IN (US); Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 16/144,301

(22) Filed: Sep. 27, 2018

(65) Prior Publication Data

US 2019/0309491 A1 Oct. 10, 2019

Related U.S. Application Data

(60) Provisional application No. 62/655,809, filed on Apr. 10, 2018, provisional application No. 62/655,223, filed on Apr. 9, 2018.

(51) Int. Cl.
*E01F 15/04* (2006.01)
*G08B 21/18* (2006.01)
(Continued)

(52) U.S. Cl.
CPC .......... *E01F 15/0438* (2013.01); *E01F 9/669* (2016.02); *E01F 13/02* (2013.01);
(Continued)

(58) Field of Classification Search
CPC ....... E01F 15/088; E01F 15/00; E01F 15/086; E01F 15/003; E01F 13/12; E01F 15/0438;
(Continued)

(56) References Cited

U.S. PATENT DOCUMENTS 3,317,189 A * 5/1967 Rubenstein ......... E01F 15/0453
256/13.1
3,449,879 A * 6/1969 Bloom ...................... E04B 1/04
52/235

(Continued)

FOREIGN PATENT DOCUMENTS

CN 102087081 A 6/2011
CN 103815604 A 5/2014
(Continued)

OTHER PUBLICATIONS

U.S. Appl. No. 16/144,256, filed Sep. 27, 2018.

*Primary Examiner* — Abigail A Risic
(74) *Attorney, Agent, or Firm* — Christopher G. Darrow; Darrow Mustafa PC

(57) ABSTRACT

Surrogates for roadside objects, such as concrete dividers, can be used for vehicle testing. A surrogate for a concrete divider can have substantially the same size and/or shape as the concrete divider that the surrogate is mimicking. The surrogate can be configured to exhibit substantially the same characteristics as their actual counterpart concrete divider when sensed by one or more vehicle sensors (e.g., cameras, radar sensors, and/or LIDAR sensors). Such surrogates can be used to test autonomous vehicles, one or more vehicle sensors, a vehicle sensor system, and/or one or more vehicle (Continued)

system (e.g., a road departure mitigation system). The surrogates can be configured to withstand being crashed into by a test vehicle without being damaged and without damaging the test vehicle.

21 Claims, 7 Drawing Sheets

(51) Int. Cl.
*E01F 15/02* (2006.01)
*E01F 13/02* (2006.01)
*E01F 9/669* (2016.01)
*G01S 7/481* (2006.01)
*G01S 17/06* (2006.01)
*G01N 21/17* (2006.01)

(52) U.S. Cl.
CPC ...... *E01F 15/0446* (2013.01); *E01F 15/0461* (2013.01); *E01F 15/0476* (2013.01); *G01S 7/4813* (2013.01); *G01S 17/06* (2013.01); *G08B 21/18* (2013.01); *G01N 2021/1793* (2013.01)

(58) Field of Classification Search
CPC .............. E01F 15/0461; E01F 15/0476; E01F 15/0446; E01F 9/669
See application file for complete search history.

(56) References Cited

U.S. PATENT DOCUMENTS

| | | | | |
|---|---|---|---|---|
| 3,591,144 | A * | 7/1971 | Iving | E01F 15/0453 404/6 |
| 3,603,562 | A * | 9/1971 | Glaesener | E01F 15/0407 256/13.1 |
| 3,704,861 | A * | 12/1972 | Glaesener | E01F 15/0453 256/13.1 |
| 4,000,882 | A * | 1/1977 | Penton | E01F 9/669 256/13.1 |
| 4,359,737 | A | 11/1982 | Bond | |
| 6,164,865 | A * | 12/2000 | McCallum | E01F 15/086 404/6 |
| 6,666,616 | B2 * | 12/2003 | Yodock, III | E01F 15/083 256/13.1 |
| 7,547,157 | B2 * | 6/2009 | Yodock, III | E01F 15/0453 404/6 |
| 7,588,387 | B1 * | 9/2009 | Christensen | E01F 15/083 256/13.1 |
| 8,434,965 | B2 * | 5/2013 | Chae | E01F 15/003 256/13.1 |
| 2003/0113161 | A1 * | 6/2003 | Yodock, III | E01F 15/083 404/6 |
| 2007/0187661 | A1 * | 8/2007 | Cheng | E01F 15/0423 256/19 |
| 2007/0199619 | A1 * | 8/2007 | Cheng | E01F 15/0423 144/136.95 |
| 2010/0111602 | A1 * | 5/2010 | Yodock, III | E01F 15/083 404/6 |
| 2013/0017015 | A1 * | 1/2013 | Chae | E01F 15/003 404/6 |
| 2013/0108361 | A1 * | 5/2013 | Mustafa | B25B 5/101 404/6 |
| 2017/0175349 | A1 * | 6/2017 | Davis | E01F 15/086 |

FOREIGN PATENT DOCUMENTS

| | | |
|---|---|---|
| CN | 203597442 U | 5/2014 |
| CN | 108278929 A | 7/2018 |
| DE | 102011006840 A1 | 10/2012 |
| RU | 2495357 C2 | 10/2013 |

* cited by examiner

SURROGATE FOR CONCRETE DIVIDER

CROSS-REFERENCE TO RELATED APPLICATIONS

This application claims the benefit of U.S. Provisional Application No. 62/655,809, filed on Apr. 10, 2018, and U.S. Provisional Application No. 62/655,223, filed on Apr. 9, 2018, both of which are incorporated herein by reference in their entirety.

FIELD

The subject matter described herein relates in general to vehicles and, more particularly, to the testing of vehicle systems.

BACKGROUND

When a vehicle departs from a road, the situation can quickly become extremely dangerous. For instance, there are various roadside objects that a vehicle can collide with, and/or the vehicle may be prone to rollover on grass. Some vehicles are equipped with a road departure mitigation system, and it is expected that the use of such systems will increase in the future. A road departure mitigation system can detect when a vehicle is about to leave the road. In such case, the road departure mitigation system can provide a warning to the driver and/or can automatically control one or more vehicle systems (e.g., steering and/or braking) to prevent the vehicle from departing the road.

SUMMARY

In one respect, the subject matter described herein is directed to a concrete divider surrogate. The concrete divider surrogate includes a main body. The main body can be substantially the same size and shape as a main body of a concrete divider. The main body can including a core, and a skin attached to the core. The core can be a non-concrete core. The skin can cover at least a portion of the core. The skin can be configured to exhibit substantially the same characteristics as the main body of the concrete divider relative to one or more vehicle sensors (e.g., camera(s), radar sensor(s), and/or LIDAR sensor(s)).

In another respect, the subject matter described herein is directed to a concrete divider surrogate. The concrete divider surrogate can include a main body, one or more posts operatively connected to the main body, and one or more base elements operatively connected to the posts. The main body can include a core, and a skin attached to the core. The skin can cover at least a portion of the core. The skin can be made of a plurality of layers. The skin can be configured to exhibit substantially the same characteristics as a concrete divider relative to one or more vehicle sensors (e.g., camera(s), radar sensor(s), and/or LIDAR sensor(s)). The concrete divider surrogate can include one or more support elements operatively connected to the main body. The main body and the one or more support elements can be separable from each other, such as when impacted by a vehicle.

DETAILED DESCRIPTION

Figure 1:
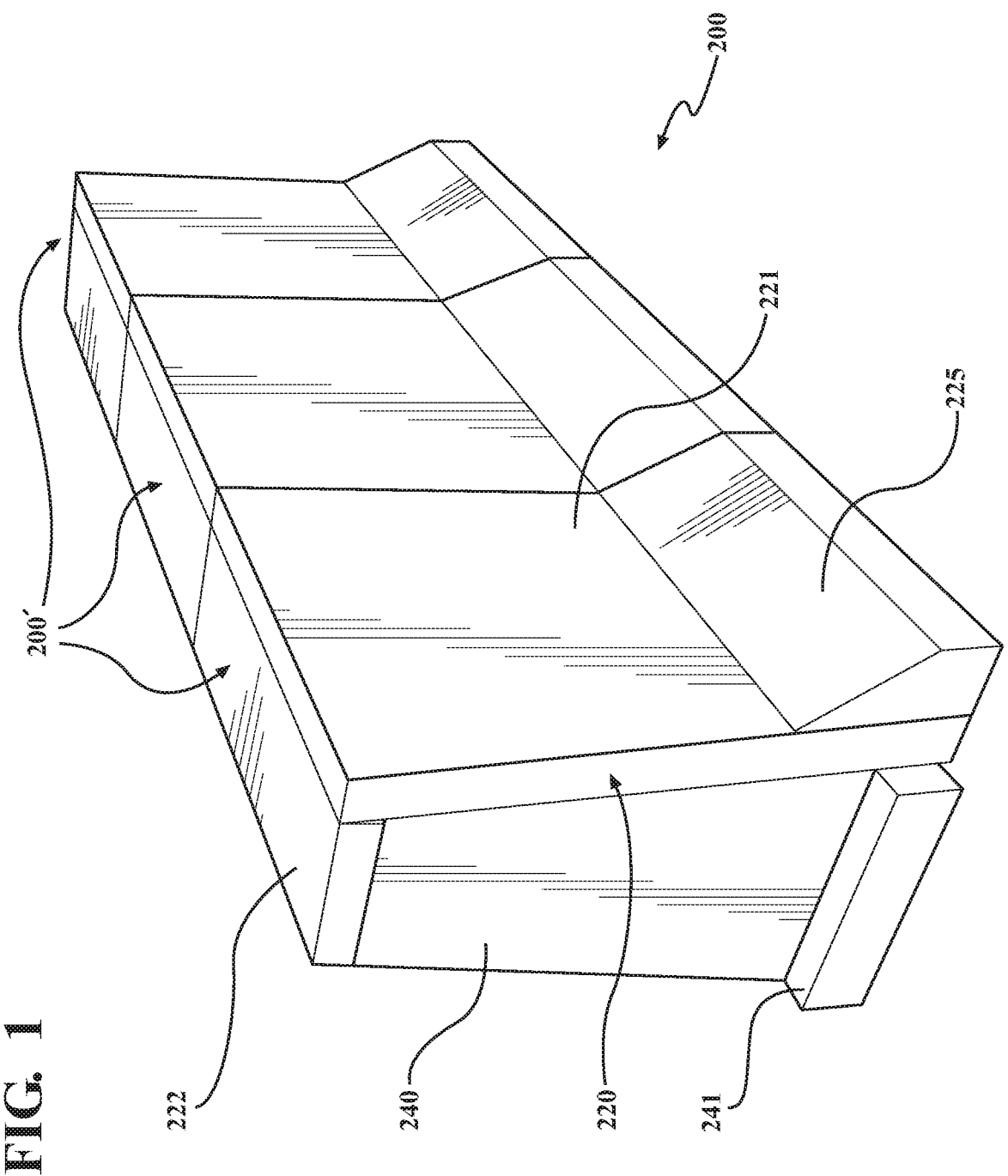
FIG. 1 is a view of an example of a divider surrogate.

According to arrangements herein, surrogates are provided for one or more roadside objects, such as a concrete divider. These surrogates can approximate the overall visual appearance of the corresponding roadside object, and they can mimic the characteristics of the corresponding roadside object relative to vehicle sensors. These surrogates can be used in the testing of vehicles, such as autonomous vehicles and/or vehicles with a road departure mitigation system.

The surrogates can be relatively lightweight, soft, and sturdy. The surrogates can be configured to be crashed into by a vehicle without damaging the test vehicle. The surrogates can also be configured to be crashed into by a vehicle without damaging the surrogate in many cases. However, it will be appreciated that, in at least some instances, damage to the surrogate may occur if it is repeatedly crashed into by a vehicle (assuming it is not rolled over by the vehicle) and/or if it is crashed into by a vehicle at high speeds. The surrogates can have substantially the same size and/or shape as the roadside objects that they are being used as a substitute. At least a portion of the surrogates can be configured to separate after being impacted by a vehicle. The surrogates can be configured to be reset for use within a period of time, such as 2 minutes or less per meter of the length of the surrogate.

The surrogates can be configured to exhibit substantially the same characteristics to one or more vehicle sensors (e.g., cameras, radar sensors, LIDAR sensors, etc.) as their corresponding roadside object. For example, the surrogates can have substantially the same visual appearance (e.g., color, size, and shape) as the corresponding roadside object. In this respect, the surrogate can appear substantially same to vehicle cameras as the actual corresponding roadside object. Further, the surrogates can exhibit substantially the same radar reflectivity and/or radar cross-section as the corresponding roadside object. In one or more arrangements, the surrogates can exhibit substantially the same radar cross-section for 24 GHz radar and/or for 77 GHz radar as the corresponding roadside object. For a concrete divider surrogate, the radar reflectivity of a skin of the concrete divider surrogate can be substantially the same as a corresponding real concrete divider for both 24 GHz and 77 GHz radar. In one non-limiting example, the radar reflectivity of a skin of the concrete divider surrogate can be −7.30±1 dB for both 24 GHz and 77 GHz radar. However, it will be understood that the radar reflectivity of a skin of the concrete divider surrogate may have other values for both 24 GHz and 77 GHz radar, depending on the particular concrete divider that is being mimicked by the surrogate. Thus, the surrogate can appear substantially the same to a radar sensor as the corresponding roadside object. Still further, the surrogates can exhibit substantially the same infrared reflectivity as the corresponding roadside object. More particularly, the surrogates can exhibit substantially the same infrared reflectivity as the corresponding roadside object at a reflectance angle of from substantially 20 degrees to substantially 70 degrees (where 0 degree is the direction normal to the object surface). The surrogate can appear substantially the same to a LIDAR sensor as the corresponding roadside object.

Figure 2:
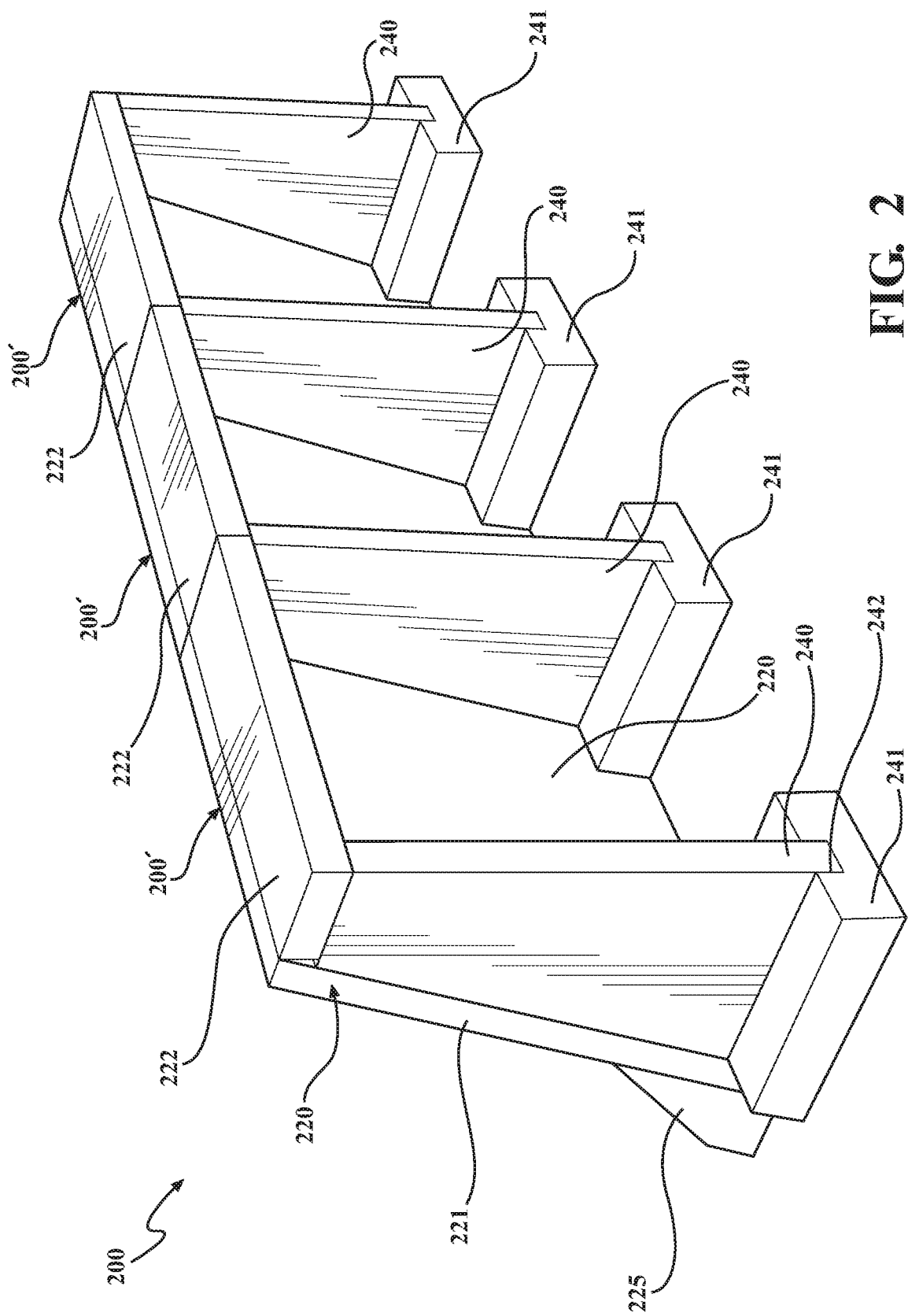
FIG. 2 is another view of the divider surrogate of FIG. 1.
Figure 3:
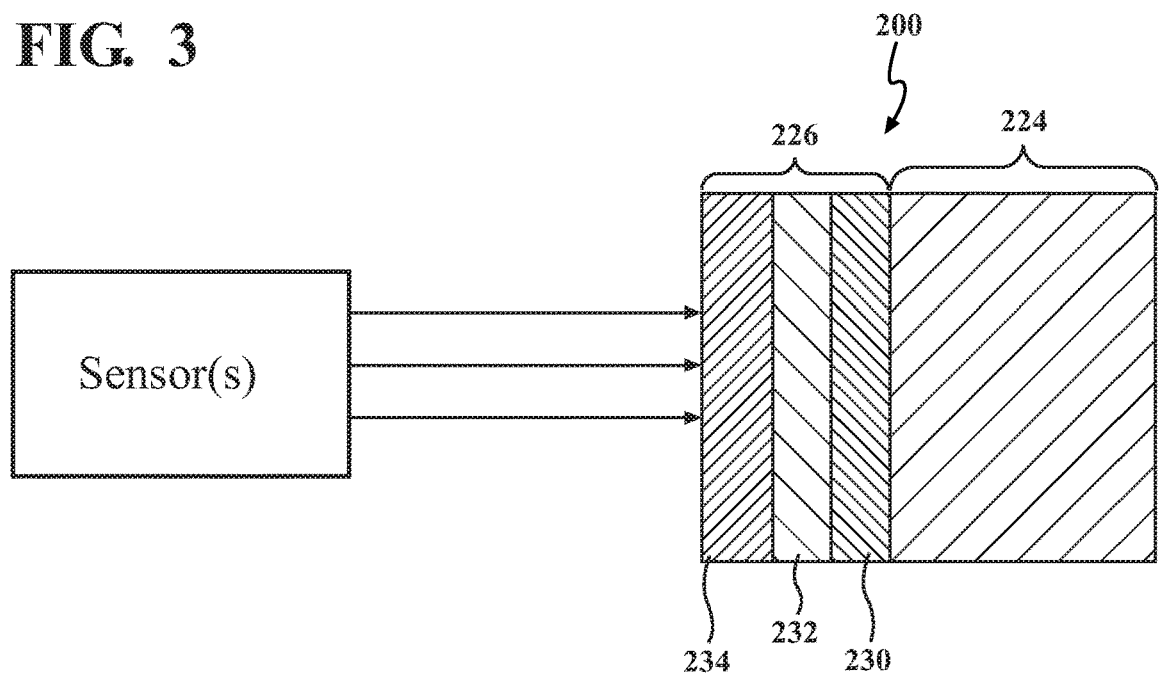
FIG. 3 is a cross-sectional view of a portion of a main body of a divider surrogate, showing a core and a multi-layer skin.

Detailed embodiments are disclosed herein; however, it is to be understood that the disclosed embodiments are intended only as exemplary. Therefore, specific structural and functional details disclosed herein are not to be interpreted as limiting, but merely as a basis for the claims and as a representative basis for teaching one skilled in the art to variously employ the aspects herein in virtually any appropriately detailed structure. Further, the terms and phrases used herein are not intended to be limiting but rather to provide an understandable description of embodiments and aspects herein. Arrangements are shown in FIGS. 1-3, but the embodiments are not limited to the illustrated structure(s) or application(s).

For purposes of simplicity and clarity of illustration, elements shown in the figures have not necessarily been drawn to scale. For example, the dimensions of some of the elements may be exaggerated relative to other elements for clarity. Further, where considered appropriate, reference numbers are repeated among the figures to indicate corresponding, analogous, or like features. In addition, numerous specific details are set forth in order to provide a thorough understanding of the embodiments described herein. However, it will be understood by those of ordinary skill in the art that the embodiments described herein can be practiced without these specific details.

As used herein, the terms "substantially" and "about" includes exactly the term they modify and slight variations therefrom. Thus, the term "substantially vertically" means exactly vertically and slight variations therefrom. Slight variations therefrom can include being within 15 degrees/units or less, 10 degrees/units or less, 9 degrees/units or less, 8 degrees/units or less, 7 degrees/units or less, 6 degrees/units or less, 5 degrees/units or less, 4 degrees/units or less, 3 degrees/units or less, 2 degrees/units or less, 1 degree/unit or less. Slight variations therefrom can include being within normal manufacturing tolerances.

Figure 4:
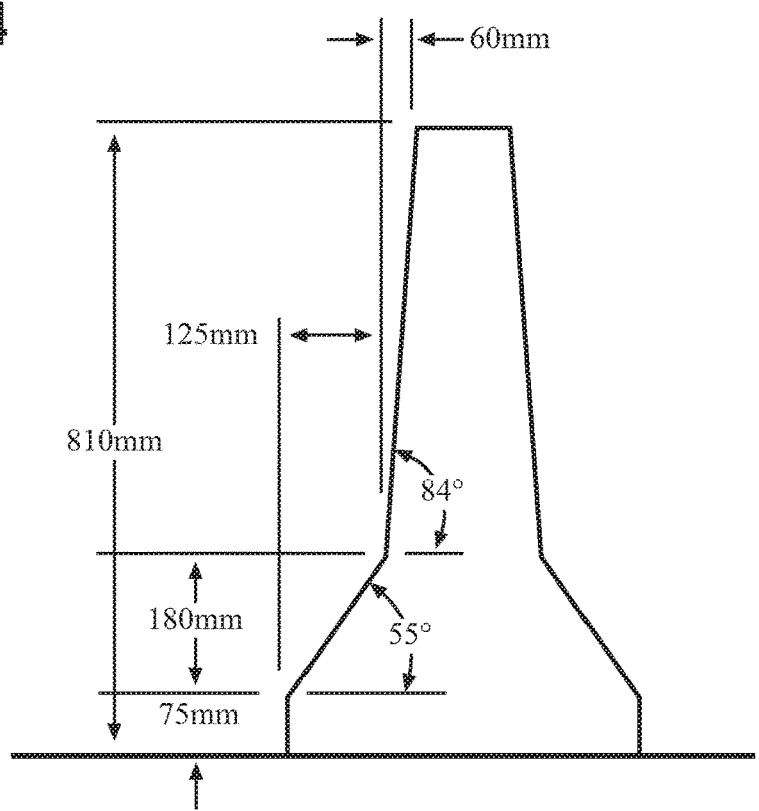
FIG. 4 is an example of a conventional F-shaped concrete divider, showing an example of the dimensions of the divider.
Figure 5A:
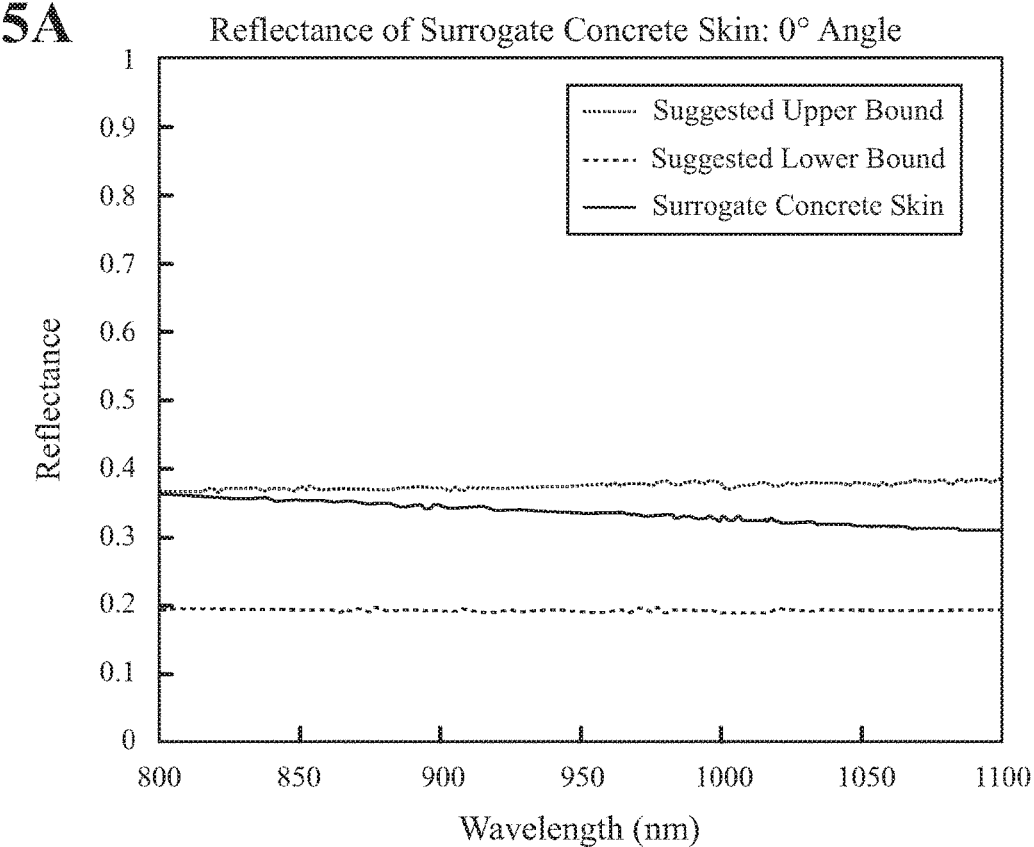
FIGS. 5A-5H show infrared reflectance test results of a divider surrogate at various detection angles.
Figure 5B:
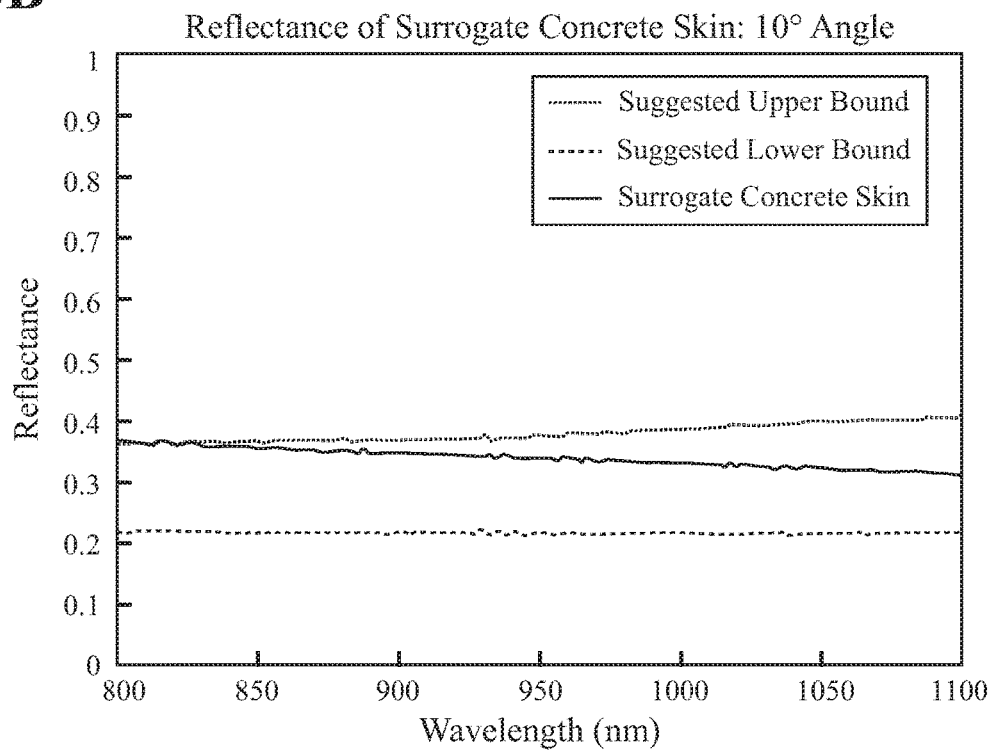
Figure 5C:
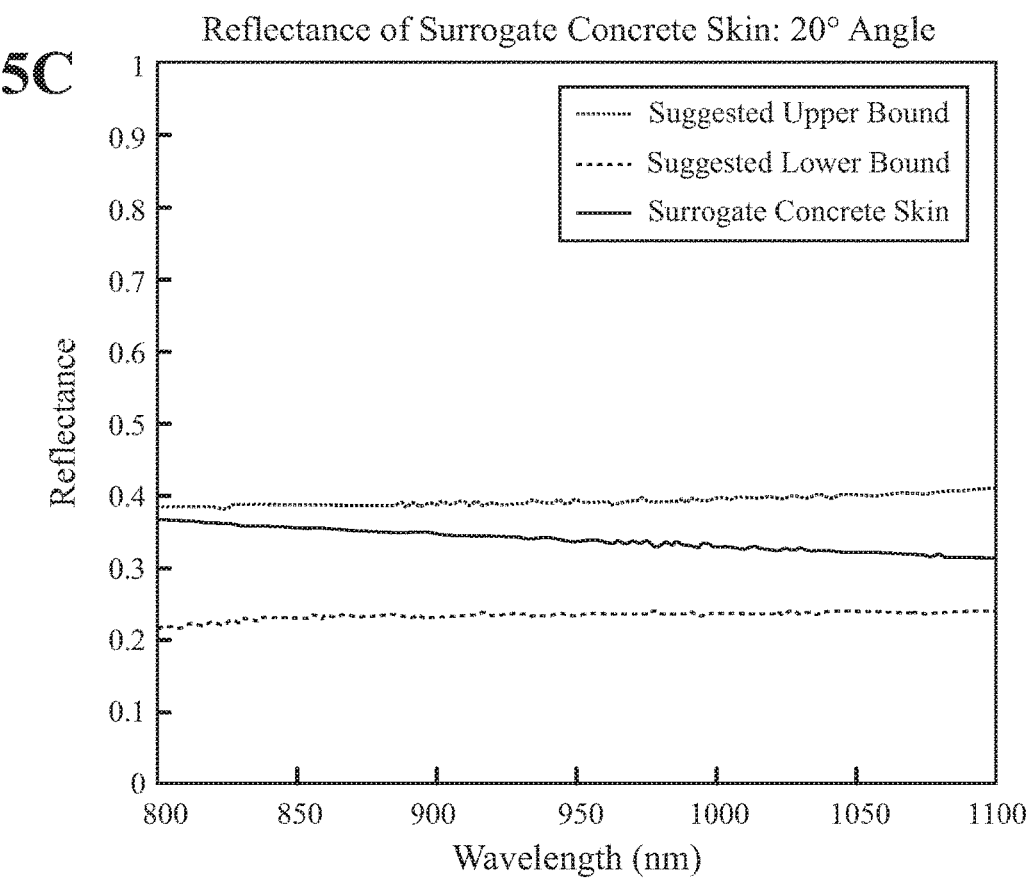
Figure 5D:
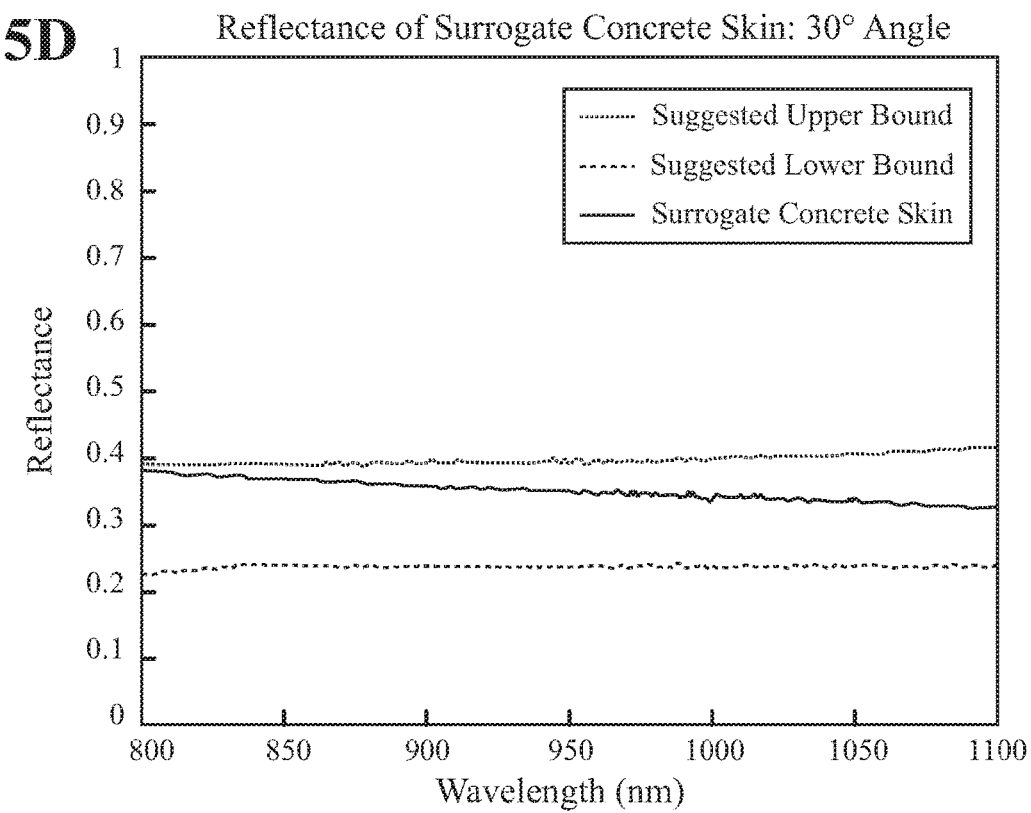
Figure 5E:
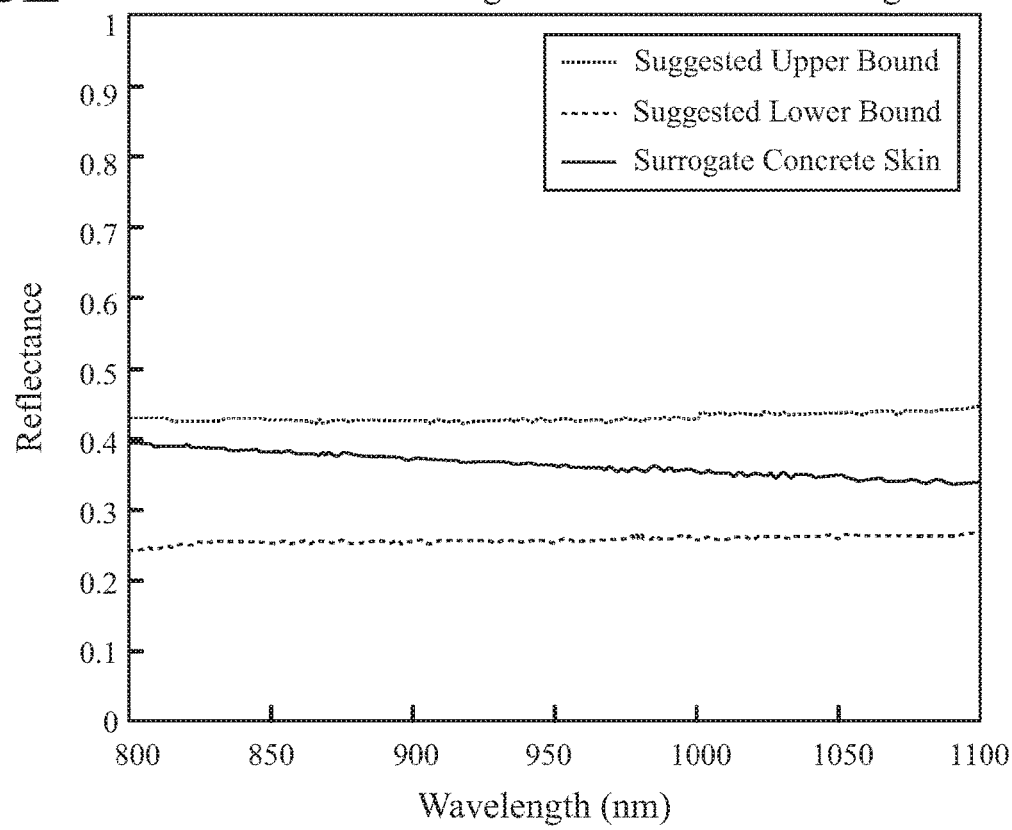
Figure 5F:
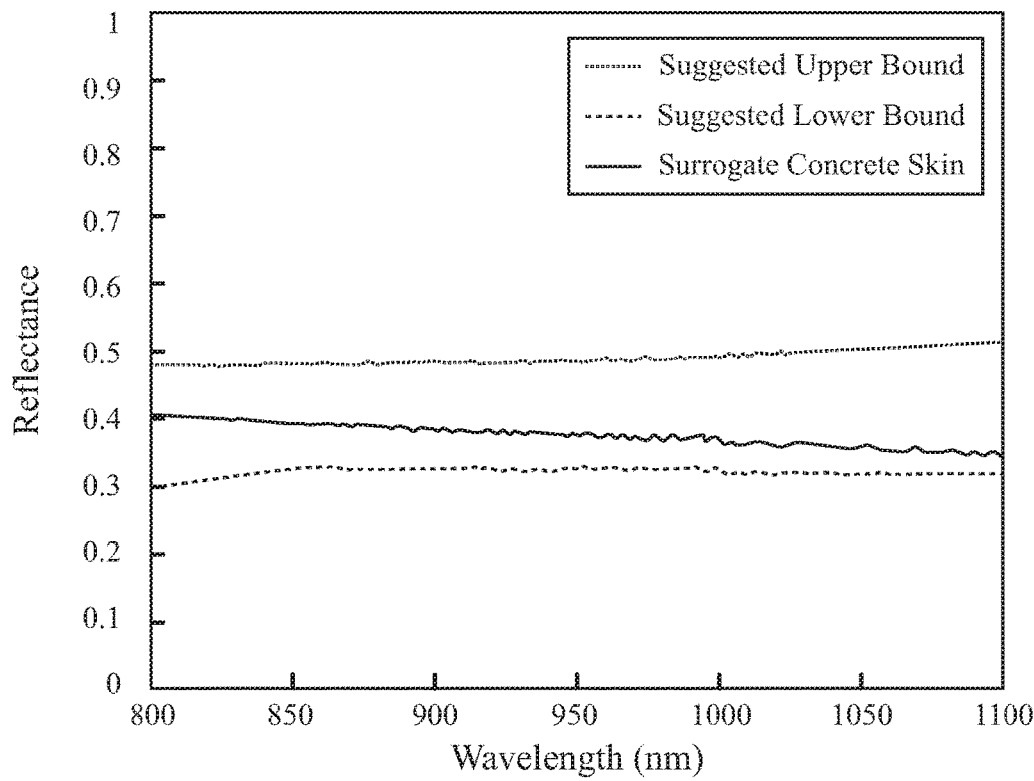
Figure 5G:
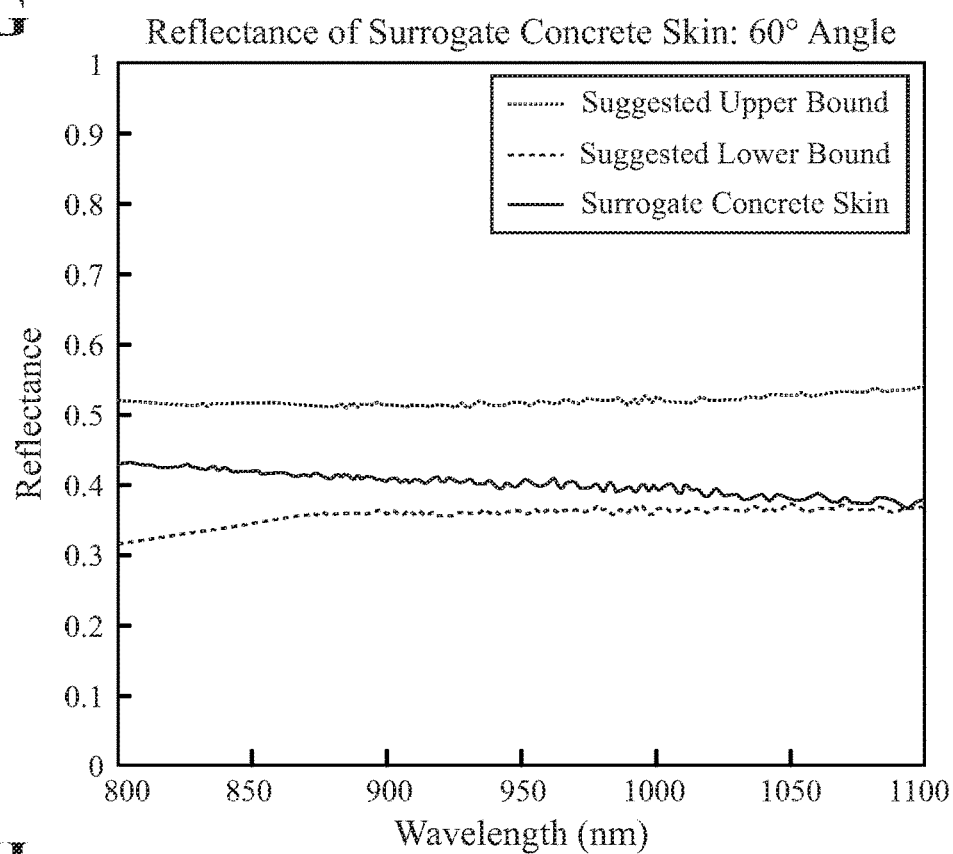
Figure 5H:
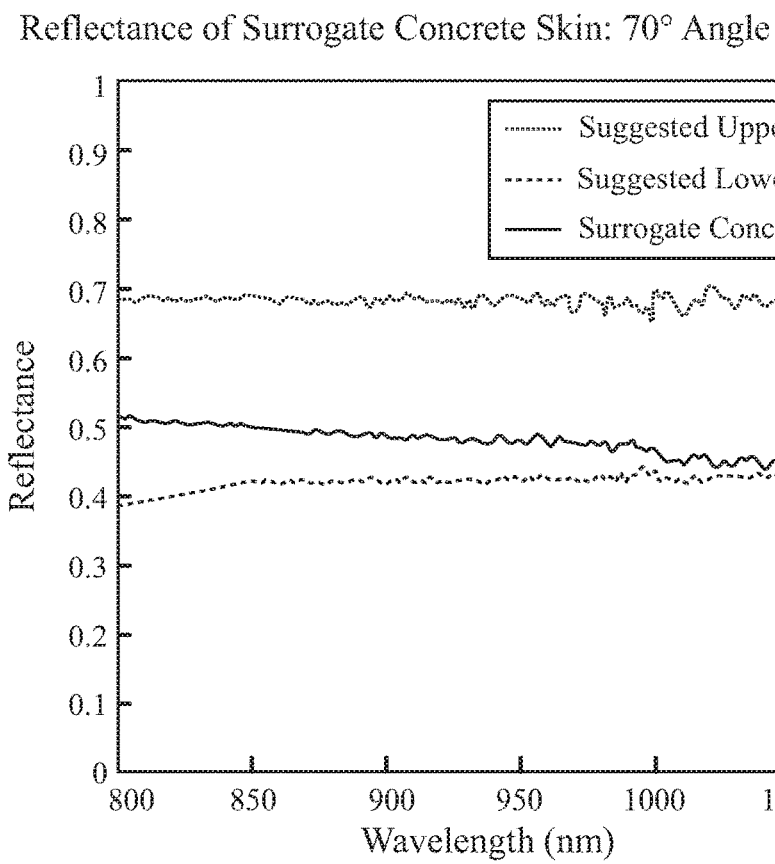

One example of a roadside object in which arrangements described herein can be used is a concrete divider. In some instances, dividers can be used as a barrier in the median of a road, such as to prevent vehicles from veering off the road into oncoming traffic. In other instances, dividers can be used to prevent a vehicle straying into a dangerous or off-limits areas, such as in construction zones. Dividers are relatively abundant on roads throughout the United States and in other countries. Dividers can be made of one or more materials, such as concrete. One of typical shapes for such dividers is referred to as an F-shape (see, e.g., FIG. 4).

In one or more arrangements, a surrogate for a concrete divider can be provided. An example of a divider surrogate 200 is shown in FIGS. 1-2. The divider surrogate 200 can have substantially the same size, shape, and/or configuration as any divider, now known or later developed. The divider surrogate 200 can have a main body 220 and one or more support elements 240. Each of these various components of the divider surrogate will be discussed in turn below.

In one or more arrangements, the main body 220 can include a major body portion 221, a top portion 222, and/or a foot portion 225. The major body portion 221, the top portion 222, and/or the foot portion 225 can be separate components. However, in some instances, any combination of these components can be formed a single piece. The major body portion 221 can have an associated inclination angle, that is, the angle of the major body portion 221 relative to vertical. As an example, the major body portion 221 can have an inclination angle of about 6 degrees relative to vertical.

The main body 220 (e.g., the major body portion 221, the top portion 222, and/or the foot portion 225) can have substantially the same size, shape, and/or configuration as the main body portion of any divider, now known or later developed. The main body 220 can have any suitable cross sectional shape. In one or more arrangements, the main body 220 can have an F-shaped configuration. However, it will be understood that the main body 220 can have other shapes corresponding to the shapes of dividers, such as New Jersey shape, single slope shape, and vertical shape.

Referring to FIG. 3, the main body 220 can include a core 224 and a skin 226. The core 224 can be made of a relatively soft, sturdy, and/or lightweight material. The core 224 can define the overall shape of the divider surrogate. For instance, the core 224 can be made of a foam material. As an example, the core 224 can be made of polyethylene foam. As an example, the core 224 can be made of 2 lb/ft³ cross-linked polyethylene foam. The core 224 can be made of a non-concrete material. The core 224 can have any suitable thickness. In one or more arrangements, the core 224 can be about 2 inches thick.

At least a portion of the core 224 can be substantially covered by the skin 226. The skin 226 can protect the underlying core 224. The skin 226 can be configured to cause the divider surrogate 200 to satisfy the requirements of one or more vehicle sensors. For instance, the skin 226 can be configured to satisfy requirements for LIDAR sensors, radar sensors, and/or cameras of a vehicle.

In one or more arrangements, the skin 226 can be made of a single layer. In one or more arrangements, the skin 226 can include a plurality of layers. For instance, in one or more arrangements, the skin 226 can include a first layer for satisfying the requirements for one or more types of vehicle sensors, and the skin 226 can include a second layer for satisfying the requirements for one or more types of vehicle sensors. The one or more vehicle sensors associated with the first layer can be different from the one or more vehicle sensors associated with the second layer. As an example, the skin 226 can include a first layer for satisfying the requirements for vehicle cameras and/or vehicle LIDAR sensors, and the skin 226 can include a second and/or a third layer for satisfying the requirements for vehicle radar sensors. In one or more arrangements, the first layer can be an outermost layer of the skin 226, and the third layer can be an innermost layer of the skin 226. The terms "outermost" and "innermost" are used for convenience relative to the core 24 of the divider surrogate 200. In some arrangements, there can be one or more intermediate layers between the outermost layer and the innermost layer. The skin 226 can also serve as a protective layer to the core 224, such as when the divider surrogate 200 is crashed into by a vehicle during testing.

In one or more arrangements, one or more layers of the skin 226 can be made of a film. The film can be made of any suitable material. For instance, in one or more arrangements, one or more layers of the skin 226 can be made of polycarbonate film. More particularly, one or more layers of the skin can be made of a matte polycarbonate film. That is, at least one of the sides of the polycarbonate film can have a matte finish. In one or more arrangements, both sides of the polycarbonate film can have a matte finish. The polycarbonate film can have any suitable thickness. For instance, the polycarbonate film can have a thickness about 0.02 inches. In one or more arrangements, the polycarbonate film can define an intermediate layer of the skin 226.

In one or more arrangements, one or more of the layers of the skin 226 can include paint. As an example, the paint can be an acrylic paint and/or a conductive paint. In some instances, the paint can be mixed with other materials. For instance, the paint can be mixed with cement (e.g., Portland cement).

In one or more arrangements, the core 224 can be covered by a fabric material. For instance, the fabric material can be made of a non-conductive fabric, such as a polyester fabric. The fabric material can minimize damage to the foam due when crashed into by a vehicle and/or due to sun exposure. The fabric material may be used on portions of the divider surrogate 200 that are not visible relative to a vehicle. For instance, the fabric material can be covered by acrylic paint. In one or more arrangements, the core 224 can be painted. The paint can minimize damage to the foam due to sun exposure.

Some examples of the skin 226 will now be provided. In one example, the skin 226 can include three layers: an outermost layer 234, an intermediate layer 232, and an innermost layer 230, as is shown in FIG. 3. The outermost layer 234 can be formed by a mixture of paint and cement. As an example, the outermost layer 234 can include concrete colored acrylic paint mixed with cement. The outermost layer 234 can have any suitable thickness. As an example, the outermost layer 234 and innermost layer 230 can have a thickness of about 50 μm to about 60 μm. These materials can satisfy the LIDAR, radar and/or camera requirements of the divider surrogate.

The intermediate layer 232 can be formed by a polycarbonate film. The polycarbonate film can be a matte-matte-polycarbonate film to facilitate paint attachment. The intermediate layer 232 can have any suitable thickness. For instance, the intermediate layer 232 can have a thickness of about 475 μm or about 0.02 inches. The innermost layer 230 can be formed by a mixture of acrylic paint and conductive carbon paint. These paints can be mixed at any suitable ratio. In one or more arrangements, the ratio of acrylic paint to the conductive paint can be about 8:1. In some implementations, two or more coats of this paint mixture can be applied. The innermost layer 230 can have any suitable thickness. For instance, the innermost layer 230 can have a thickness of about 50 μm to about 60 μm. The innermost layer 230 can help in satisfying the radar sensor requirement. The thickness of the layers can be adjusted to satisfy radar requirements.

In another example, the outermost layer 234 of the skin 226 can be formed by a mixture of paint and cement. For instance, the outermost layer can include concrete colored acrylic paint mixed with Portland cement. These materials can be mixed at any suitable ratio. In one or more arrangements, the ratio of acrylic paint to Portland cement can be about 32:1. The outermost layer 234 can have any suitable thickness. As an example, the outermost layer can have a thickness of about 50 μm to about 100 μm. These materials can satisfy the LIDAR and/or camera requirements of the divider surrogate.

The intermediate layer 232 can be formed by a polycarbonate film. The polycarbonate film can be a matte-matte-polycarbonate film to facilitate paint attachment. The intermediate layer 232 can have any suitable thickness. For instance, the intermediate layer 232 can have a thickness of about 0.02 inches. The innermost layer 230 can be formed by a mixture of acrylic paint and carbon paint. These paints can be mixed at any suitable ratio. In one or more arrangements, the ratio of acrylic paint to carbon paint can be about 8:1. In some implementations, two or more coats of this paint mixture can be applied. The innermost layer 230 can have any suitable thickness. For instance, the innermost layer 230 can have a thickness of about 50 μm to about 100 μm. The intermediate layer and innermost layer 230 can help in satisfying the radar sensor requirement. The thickness of the layers can be adjusted to satisfy radar requirements.

The skin 226 can be attached to the core 224 in any suitable manner. For instance, the skin 226 can be attached to the core 224 by one or more adhesives and/or one or more fasteners. In one or more arrangements, the skin 226 can be attached to the core 224 using tape. In one or more arrangements, the skin 226 can be attached to the core 224 using hook and loop type fasteners (e.g., Velcro).

The divider surrogate 200 can include one or more support elements 240, as is shown in FIGS. 1-2. The support elements 240 can be made of any suitable material, such as a material that does not substantially affect the radar reflectivity of the skin 226. For instance, the support elements 240 can be made of foam. The support elements 240 can have any suitable configuration. For instance, one or more of the support elements 240 can be substantially rectangular, triangular, or trapezoidal in shape. In one or more arrangements, the support elements 240 can have a tripod configuration. The one or more support elements 240 can contact and/or can be operatively connected to one or more portions of the main body 220 (e.g., the major body portion 221 and/or the top portion 222).

When the divider surrogate 200 includes a plurality of support elements 240, the support elements 240 can be substantially identical to each other. Alternatively, one or more support elements 240 can be different from the other support elements 240 in one or more respects.

In one or more arrangements, a bottom portion of the support elements 240 can be supported directly on the ground. In one or more arrangements, a bottom portion of one or more of the support elements 240 can be received in a respective base 241 (FIG. 1). In some instances, one or more of the support elements 240 may not be associated with a base 241. The base(s) 241 can have any suitable configuration. The base(s) 241 can help to support and/or stabilize the divider surrogate 200. When the divider surrogate 200 includes a plurality of bases 241, the bases 241 can be substantially identical to each other. Alternatively, one or more bases 241 can be different from the other bases 241 in one or more respects.

In one or more arrangements, the main body 220 of the divider surrogate 200 can include a foot portion 225. When the divider surrogate 200 includes the foot portion 225, it can be considered to have an F-shaped or New Jersey configuration. The foot portion 225 can be formed with the main body 220 as a single structure. For instance, the foot portion 225 can be formed with the major body portion 221. Alternatively, the foot portion 225 can be formed as a separate piece and operatively connected to the main body 220, such as to the major body portion 221.

The divider surrogate 200 can be formed by a plurality of main body segments 220' (FIG. 1). The main body segments 220' can be operatively connected in an end to end manner. In one or more arrangements, the main body segments 220' can have a height of about 32 inches and a length of about 4.5 feet. However, it will be appreciated that these dimensions are merely one example, as the main body 220 of the divider surrogate 200 can have different heights and/or lengths. Of course, it will be understood that the main body 220 of the divider surrogate 200 can be a single piece. The major body portion 221 can have an inclination angle of about 6 degrees from vertical, but other inclination angles are possible.

One example arrangement of the divider surrogate 200 will be described in connection with FIG. 3. In this example, the core 224 of the main body 220 can be made of cross-linked polyethylene foam, and the skin 226 of the main body 220 can have three layers. An outermost layer 234 can be made of a 32:1 mix of concrete colored acrylic paint and Portland cement. This mix of paint and cement can be applied in one or more layers. An intermediate layer 232 can be made of about 0.01 to about 0.2 inch thick polycarbonate film. In one or more arrangements, the polycarbonate film can be about 0.01 inches thick, about 0.02 inches thick, or about 0.5 inches thick. In one or more arrangements, the polycarbonate film can be a matte-matte polycarbonate film. An innermost layer 230 can be made of 8:1 mix of acrylic paint and conductive carbon paint. In one or more arrangements, this mix of paint can be applied in two coats. In testing, the divider surrogate 200 met camera requirements, radar reflectivity requirements (e.g., $-7.3 \pm 1$ dB for both 24 GHz and 77 GHz radar), and infrared requirements for 20 to 70 degrees. Test data also showed that the divider surrogate 200 also met infrared requirements in the detection angle range of 0 to 70 degrees, as is shown in FIGS. 5A-5H.

In one or more arrangements, the skin 226 can include concrete colored acrylic paint mixed with cement, 0.02 inch polycarbonate film, and 8:1 ratio mixed acrylic paint and conductive carbon paint. In one or more arrangements, the skin 226 can include latex paint on polycarbonate sheet. In one or more arrangements, the skin 226 can include 32:1 mix of concrete colored acrylic paint and Portland cement, polycarbonate film (matte-matte film, 0.2 inches thick), and 8:1 mix of acrylic paint and conductive carbon paint.

While a divider surrogate has been described above, it will be understood that the approaches described herein can generally be applied to create surrogates for other roadside objects, such as curbs, poles, tree trunks.

The surrogates described herein can be used for various purposes. For instance, the surrogates can be used in connection with the testing of vehicles. The vehicle can have a sensor system. The sensor system can include one or more sensors. "Sensor" means any device, component and/or system that can detect, determine, assess, monitor, measure, quantify and/or sense something. The one or more sensors can detect, determine, assess, monitor, measure, quantify and/or sense in real-time. As used herein, the term "real-time" means a level of processing responsiveness that a user or system senses as sufficiently immediate for a particular process or determination to be made, or that enables the processor to keep up with some external process.

In arrangements in which the sensor system includes a plurality of sensors, the sensors can work independently from each other. Alternatively, two or more of the sensors can work in combination with each other. In such case, the two or more sensors can form a sensor network. The sensor system and/or the one or more sensors can be operatively connected to processor(s), the data store(s), and/or other elements or systems of the vehicle. The sensor system can acquire data of at least a portion of the external environment of the vehicle.

The sensor system can include one or more environment sensors 123 configured to acquire, detect, determine, assess, monitor, measure, quantify and/or sense driving environment data. "Driving environment data" includes and data or information about the external environment in which a vehicle is located or one or more portions thereof. For example, the one or more environment sensors can acquire data or information about obstacles in at least a portion of the external environment of the vehicle. In one or more arrangements, the sensor system can include one or more radar sensors, one or more LIDAR sensors, and/or one or more cameras.

The surrogates can be used on a test track or testing facility. The surrogates can be set up in an appropriate position with respect to the road. It should be noted that the divider surrogate be used on one or both sides of a road. Divider surrogates used on one side of the road can be substantially identical to divider surrogates used on the other side of the road, or they can be substantially mirror images of each other.

The vehicle can move along the test track and the sensor system can acquire driving environment data, including data about the divider surrogate, using the camera(s), the radar sensor(s), and the LIDAR sensor(s). Due to the construction of the divider surrogate, the data of the divider surrogate acquired by the sensor system can mimic the sensor data that would be acquired by the sensor system in a real world driving environment. The vehicle can process the sensor data to determine an appropriate action. However, if for some reason, the vehicle does not detect the divider surrogate and the vehicle collides with the divider surrogate, at least some of the individual components of the divider surrogate may separate. However, due to the construction of the divider surrogate, damage to the vehicle and the divider surrogate is avoided. The divider surrogate can be readily set up again and further testing can be performed.

As an example, the surrogates described herein can be used in connection with the testing of the sensors and/or systems of an autonomous vehicle. "Autonomous vehicle" means a vehicle that configured to operate in an autonomous operational mode in which one or more computing systems are used to navigate and/or maneuver the vehicle along a travel route with minimal or no input from a human driver. In one or more arrangements, the autonomous vehicle can be highly automated or completely automated. As another example, the surrogates described herein can be used to road departure mitigation systems of non-autonomous vehicles.

It will be appreciated that arrangements described herein can provide numerous benefits, including one or more of the benefits mentioned herein. For example, arrangements described herein can provide surrogates that appear to be visually realistic to their counterpart roadside objects. Arrangements described herein can provide surrogates that mimic their corresponding roadside object with respect to one or more sensors. Arrangements described here enable the surrogates to be used in vehicle testing, particularly the testing of road departure systems. Arrangements described herein can be crashed into during testing, thereby avoiding damage to the surrogates and to the test vehicle. Arrangements described herein can be used for internal testing and to support upcoming European New Car Assessment Programme (EUNCAP) requirements for road departure systems and potential future National Highway Traffic Safety Administration (NHTSA)/Insurance Institute for Highway Safety (IIHS) requirements.

The terms "a" and "an," as used herein, are defined as one or more than one. The term "plurality," as used herein, is defined as two or more than two. The term "another," as used herein, is defined as at least a second or more. The terms "including" and/or "having," as used herein, are defined as comprising (i.e. open language). The phrase "at least one of . . . and . . . " as used herein refers to and encompasses any and all possible combinations of one or more of the associated listed items. As an example, the phrase "at least one of A, B and C" includes A only, B only, C only, or any combination thereof (e.g. AB, AC, BC or ABC).

Aspects described herein can be embodied in other forms and combinations without departing from the spirit or essential attributes thereof. Thus, it will of course be understood that embodiments are not limited to the specific details described herein, which are given by way of example only, and that various modifications and alterations are possible.

What is claimed is:

1. A concrete divider surrogate comprising:
    a main body, the main body configured to be substantially the same size and shape as a main body of a concrete divider, the main body including a core and a skin attached to the core, the skin covering at least a portion of the core, the skin including a plurality of layers, the plurality of layers including a first layer, a second layer, and an intermediate layer, the intermediate layer being located between the first layer and the second layer, wherein at least one of:
        the first layer includes a mixture of paint and cement; and
        the second layer includes a conductive material.

2. The concrete divider of claim 1, wherein the main body is made of a plurality of main body segments, and wherein the main body segments are operatively connected in an end to end manner.

3. The concrete divider surrogate of claim 1, wherein the core is made of a foam material.

4. The concrete divider surrogate of claim 1, wherein an outermost layer of the plurality of layers is configured to exhibit substantially the same characteristics as a concrete divider relative to a camera or a LIDAR sensor.

5. The concrete divider surrogate of claim 1, wherein the plurality of layers is configured to collectively exhibit substantially the same characteristics as a concrete divider relative to a RADAR sensor.

6. The concrete divider surrogate of claim 1, wherein the first layer includes a mixture of paint and cement.

7. The concrete divider surrogate of claim 6, wherein the first layer defines an outermost layer of the plurality of layers of the skin.

8. The concrete divider surrogate of claim 1, wherein the second layer defines an innermost layer of the plurality of layers of the skin, and wherein includes a mixture of acrylic paint and conductive carbon paint.

9. The concrete divider surrogate of claim 1, wherein the intermediate layer includes polycarbonate film.

10. The concrete divider surrogate of claim 1, further including one or more support elements operatively connected to the main body.

11. A concrete divider surrogate comprising:
    a main body, the main body including a core and a skin attached to the core, the skin covering at least a portion of the core, the skin including a plurality of layers, the plurality of layers including a first layer, a second layer, and an intermediate layer, the intermediate layer being located between the first layer and the second layer, wherein at least one of:
        the first layer includes a mixture of paint and cement, and
        the second layer includes a conductive material; and
    one or more support elements operatively connected to the main body, the main body and the one or more support elements being separable from each other.

12. The concrete divider surrogate of claim 11, wherein the first layer a mixture of paint and cement, and wherein the second layer includes a mixture of acrylic paint and conductive carbon paint.

13. The concrete divider surrogate of claim 12, wherein the first layer defines an outermost layer of the skin, and wherein the second layer defines an innermost layer of the skin.

14. The concrete divider surrogate of claim 12, wherein the main body is made of a plurality of segments, and wherein the segments are operatively connected in an end to end manner.

15. The concrete divider surrogate of claim 12, wherein the skin is configured to exhibit substantially the same radar cross-section as a main body of a concrete divider for at least one of 24 GHz radar or for 77 GHz radar.

16. The concrete divider surrogate of claim 12, wherein the skin is configured to exhibit substantially the same infrared reflectivity as a main body of a concrete divider a reflectance angle of from substantially 0 degrees to substantially 70 degrees.

17. A concrete divider surrogate comprising:
    a main body, the main body including a core and a skin attached to the core, the skin covering at least a portion of the core,
    the skin being made of a plurality of layers, the plurality of layers including an outermost layer, an innermost layer, and an intermediate layer,
    the intermediate layer being located between the outermost layer and the innermost layer, the outermost layer includes a mixture of paint and cement, and the innermost layer includes a mixture of acrylic paint and conductive carbon paint, and
    one or more support elements operatively connected to the main body, the main body and the one or more support elements being separable from each other.

18. The concrete divider surrogate of claim 17, wherein the intermediate layer includes a polycarbonate film.

19. A concrete divider surrogate comprising:
    a main body, the main body configured to be substantially the same size and shape as a main body of a concrete divider, the main body including a core and a skin attached to the core, the skin covering at least a portion of the core,
    the skin being made of a plurality of layers, the plurality of layers including an outermost layer, an innermost layer, and an intermediate layer, the intermediate layer being located between the outermost layer and the innermost layer,
    the outermost layer includes a mixture of paint and cement, and the innermost layer includes conductive paint.

20. A surrogate for a roadside object for use in vehicle testing, the surrogate comprising:
    a body configured to be substantially the same size and shape as a body of a roadside object, the body including a core and a skin attached to the core, the skin covering at least a portion of the core,
    the core including a foam material, and
    the skin including at least three layers, wherein:
        one of the at least three layers including a mixture of paint and cement; and
        one of the at least three layers includes a conductive material.

21. The surrogate of claim 20, wherein an outermost layer of the at least three layers includes a mixture of paint and cement, wherein an innermost layer of the at least three layers includes conductive paint, wherein an intermediate layer of the at least three layers includes polycarbonate, and wherein the intermediate layer is located between the outermost layer and the innermost layer.

* * * * *